(12) United States Patent
Kim

(10) Patent No.: US 11,191,513 B2
(45) Date of Patent: Dec. 7, 2021

(54) MOBILE X-RAY DEVICE AND METHOD FOR CONTROLLING POWER IN MOBILE X-RAY DEVICE

(71) Applicant: SAMSUNG ELECTRONICS CO., LTD., Suwon-si (KR)

(72) Inventor: Myeong Je Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 63 days.

(21) Appl. No.: 16/759,942

(22) PCT Filed: Oct. 29, 2018

(86) PCT No.: PCT/KR2018/012916
§ 371 (c)(1),
(2) Date: Apr. 28, 2020

(87) PCT Pub. No.: WO2019/088622
PCT Pub. Date: May 9, 2019

(65) Prior Publication Data
US 2020/0405253 A1    Dec. 31, 2020

(30) Foreign Application Priority Data

Nov. 1, 2017   (KR) ........................ 10-2017-0144873
Oct. 26, 2018  (KR) ........................ 10-2018-0129338

(51) Int. Cl.
*A61B 6/00* (2006.01)
*G06N 3/08* (2006.01)
*G01R 31/3835* (2019.01)

(52) U.S. Cl.
CPC .............. *A61B 6/54* (2013.01); *A61B 6/4405* (2013.01); *A61B 6/56* (2013.01); *G01R 31/3835* (2019.01)

(58) Field of Classification Search
CPC .......... A61B 6/54; A61B 6/56; A61B 6/4405; A61B 6/563; A61B 6/4411; A61B 6/44; G01R 31/3835; G06N 3/08
See application file for complete search history.

(56) References Cited

U.S. PATENT DOCUMENTS 9,277,298 B2   3/2016  Yang et al.
9,771,848 B2   9/2017  Hashimoto
(Continued)

FOREIGN PATENT DOCUMENTS

KR   10-2013-0031203   3/2013
KR   10-1348042        1/2014
(Continued)

OTHER PUBLICATIONS

International Search Report dated Feb. 8, 2019, in corresponding International Patent Application No. PCT/KR2018/012916.
(Continued)

*Primary Examiner* — Don K Wong
(74) *Attorney, Agent, or Firm* — Staas & Halsey, LLP

(57) ABSTRACT

In a mobile X-ray apparatus including a power supply supplying operation power, the power supply may include: a battery pack including a plurality of battery cells; a battery management system configured to control the operation power to be supplied from the battery pack to at least one component of the mobile X-ray apparatus; and a monitoring integrated circuit configured to monitor a voltage of the plurality of battery cells and control monitoring power supplied from the plurality of battery cells, based on whether the operation power is supplied to at least one component of the mobile X-ray apparatus.

15 Claims, 11 Drawing Sheets

(56) References Cited

U.S. PATENT DOCUMENTS

| | | |
|---|---|---|
| 10,172,586 B2 | 1/2019 | Kim |
| 10,553,911 B2 | 2/2020 | Ro |
| 2019/0307413 A1* | 10/2019 | MacLaughlin ...... A61B 6/4405 |

FOREIGN PATENT DOCUMENTS

| | | |
|---|---|---|
| KR | 10-2015-0047749 | 5/2015 |
| KR | 10-2016-0024603 | 3/2016 |
| KR | 10-2017-0078414 | 7/2017 |

OTHER PUBLICATIONS

Written Opinion of the International Searching Authority dated Feb. 8, 2019, in corresponding International Patent Application No. PCT/KR2018/012916.

* cited by examiner

MOBILE X-RAY DEVICE AND METHOD FOR CONTROLLING POWER IN MOBILE X-RAY DEVICE

CROSS-REFERENCE TO RELATED APPLICATIONS

This application is a U.S. National Stage Application which claims the benefit under 35 U.S.C. § 371 of International Patent Application No. PCT/KR2018/012916 filed on Oct. 29, 2018, which claims foreign priority benefit under 35 U.S.C. § 119 of Korean Patent Application No. 10-2017-0144873 filed on Nov. 1, 2017 and Korean Patent Application No. 10-2018-0129338 filed Oct. 26, 2018 in the Korean Intellectual Property Office, the contents of both of which are incorporated herein by reference.

TECHNICAL FIELD

The present disclosure relates to a mobile X-ray apparatus including a battery and a power control method in the mobile X-ray apparatus.

BACKGROUND ART

X-rays are electromagnetic waves generally having wavelengths of 0.01 to 100 Å and, due to their properties of penetrating objects, may be widely used in medical apparatuses for imaging the inside of a living body or in non-destructive testing equipment for industrial use.

An X-ray apparatus using X-rays may obtain X-ray images of an object by transmitting X-rays emitted from an X-ray source through the object and detecting a difference in intensities of the transmitted X-rays via an X-ray detector. The X-ray apparatus may figure out an internal structure of the object by using the X-ray image and make a diagnosis of the object. The X-ray apparatus facilitates observation of the internal structure of the object by using a principle in which the transmittance of X-rays varies depending on the density of the object and the atomic numbers of atoms constituting the object.

As a wavelength of an X-ray decreases, transmittance of the X-ray increases and brightness of an image on a screen increases.

There are two types of X-ray apparatuses: a general X-ray apparatus fixed in a certain space and a mobile X-ray apparatus that may be moved to any place.

In a mobile X-ray apparatus, an X-ray radiation device is mounted on a movable main body, and a portable X-ray detector is used. Therefore, the mobile X-ray apparatus may perform X-ray imaging in various places rather than in a specific place. Such a mobile X-ray apparatus includes a battery therein, and by charging the battery, may perform X-ray imaging in various places where power is not supplied

DESCRIPTION OF EMBODIMENTS

Solution to Problem

The present disclosure provides a mobile X-ray apparatus including a battery and a power control method of the mobile X-ray apparatus, wherein the power control method includes blocking power supplied to a monitoring integrated circuit which monitors a voltage of the battery cells when shut-down occurs in the mobile X-ray apparatus.

Advantages Effects of Disclosure

According to embodiments of the present disclosure, the mobile X-ray apparatus may determine whether a power supply of a mobile X-ray apparatus is shut down, and in response to a result of the determination, block power supplied to a monitoring integrated circuit, thereby preventing discharge of battery cells and extending a preservation period of a battery.

BRIEF DESCRIPTION OF DRAWINGS

The present disclosure will be more clearly understood by combination of the following detailed descriptions and the accompanying drawings, and reference numerals indicate structural elements.

BEST MODE

Figure 1:
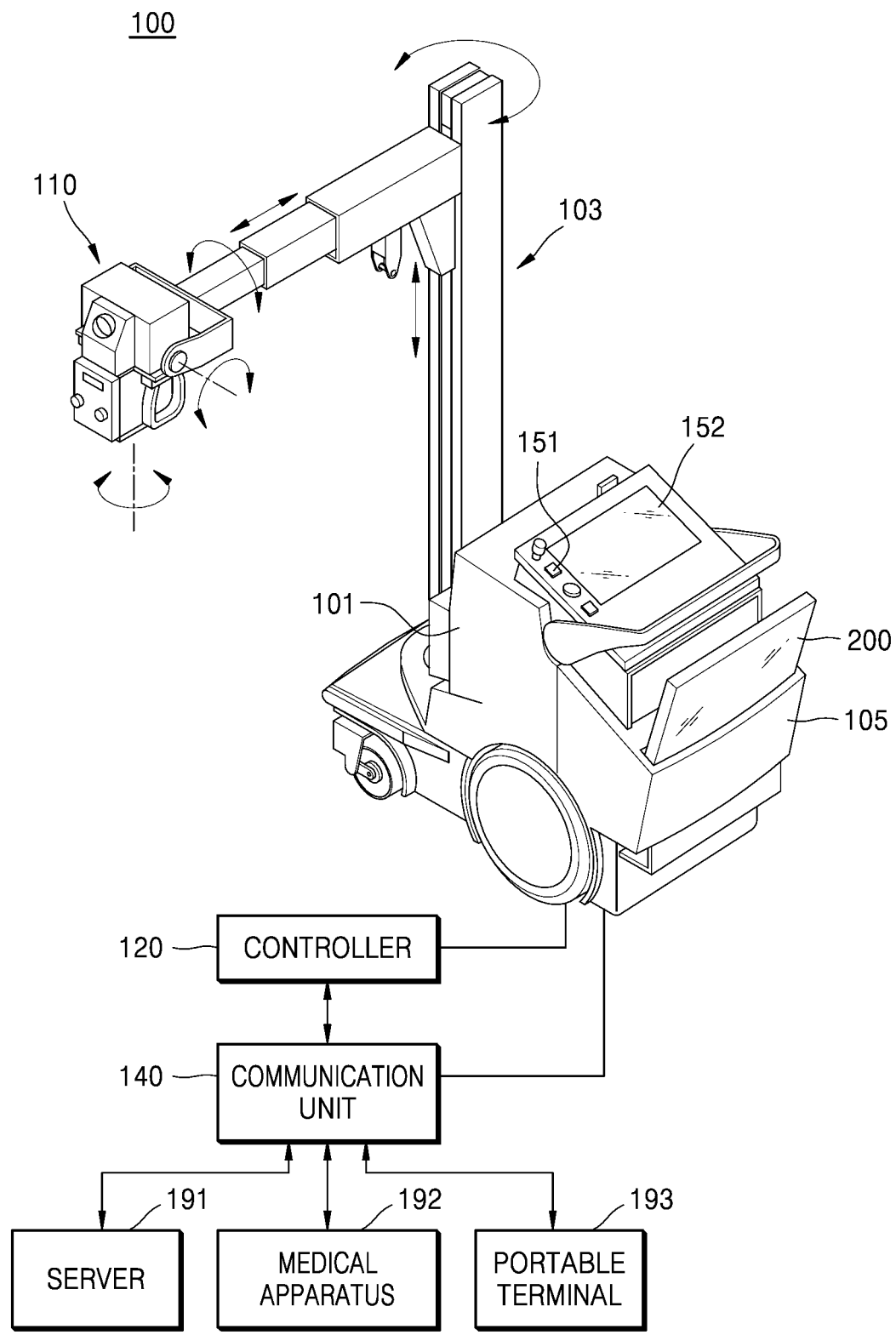
FIG. 1 is an external view of an X-ray apparatus according to an embodiment.

According to an aspect, there is provided a mobile X-ray apparatus including a power supply which supplies operation power. The power supply may include: a battery pack including a plurality of battery cells; a battery management system configured to control the operation power to be supplied from the battery pack to at least one component of the mobile X-ray apparatus; and a monitoring integrated circuit configured to monitor a voltage of the plurality of battery cells and control monitoring power, which is supplied from the plurality of battery cells, based on the operation power supplied to the at least one component of the mobile X-ray apparatus.

According to another aspect, there is provided a power control method of a mobile X-ray apparatus including a power supply, wherein the power supply includes a battery pack including a plurality of battery cells, a monitoring integrated circuit configured to monitor a voltage of the plurality of battery cells, and a battery management system, and supplies operation power. The power control method of the mobile X-ray apparatus may include: monitoring the power supply that controls the operation power to be supplied from the battery pack to at least one component of the mobile X-ray apparatus; determining whether the power supply is shut down; and in response to a result of the determination, blocking monitoring power supplied from the plurality of battery cells to the monitoring integrated circuit.

According to another aspect, provided is a recording medium having recorded thereon a program including computer-executable instructions of a power control method of the mobile X-ray apparatus.

MODE OF DISCLOSURE

Terms used in the present disclosure are general terms that are currently widely used in the technical art in consideration of functions in the present disclosure. However, the terms may be changed reflecting intensions of one of ordinary skill in the art, precedents, or new technologies. In addition, some of the terms may have been arbitrarily chosen by the applicant, and in this case, the meaning of the terms will be described in detail in the description of disclosure. Accordingly, the terms used herein will be understood based on meanings of the terms and the whole context of the present disclosure, not based on mere names.

When it is described throughout the specification that a portion "includes" a component, the portion may further include another component rather than precluding the other component unless otherwise specified.

Although the terms including ordinal numbers such as "first" and "second" may be used to describe various elements, these elements are not limited by these terms. The terms are only used to distinguish one component from another. For example, a first component may be named as a second component without exceeding the scope of the present disclosure, and similarly, the second component may also be named as the first component. The term "and/or" includes a combination of a plurality of related items or any one of the plurality of related items.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail. Terms such as "part" and "portion" used herein denote those that may be embodied by software or hardware. According to exemplary embodiments, a plurality of parts or portions may be embodied by a single unit or element, or a single part or portion may include a plurality of elements.

Hereinafter, embodiments of the present disclosure will be described in detail with reference to the accompanying drawings such that one of ordinary skill in the art may easily implement the present disclosure. However, the present disclosure may be embodied in many different forms and is not limited to embodiments described herein.

Hereinafter, embodiments will be described in detail with reference to the accompanying drawings.

FIG. 1 is an external view and block diagram of an X-ray apparatus 100 implemented as a mobile X-ray apparatus, according to an exemplary embodiment.

Referring to FIG. 1, the X-ray apparatus 100 according to the present exemplary embodiment includes an X-ray radiation device for generating and emitting X-rays, an input device 151 for receiving a command from a user, a display 152 for providing information to the user, a controller 120 for controlling the X-ray apparatus 100 according to the received command, and a communication unit 140, i.e., a communication device or interface, for communicating with an external device.

The X-ray radiation device 110 may include an X-ray source for generating X-rays and a collimator for adjusting a region irradiated with the X-rays generated by the X-ray source.

When the X-ray apparatus 100 is implemented as a mobile X-ray apparatus, a main body 101 connected to the X-ray radiation device 110 is freely movable, and an arm 103 connecting the X-ray radiation device 110 and the main body 101 to each other is rotatable and linearly movable. Thus, the X-ray radiation device 110 may be moved freely in a three-dimensional (3D) space.

The input device 151 may receive commands for controlling imaging protocols, imaging conditions, imaging timing, and locations of the X-ray radiation device 110. The input device 151 may include a keyboard, a mouse, a touch screen, a microphone, a voice recognizer, etc.

The display 152 may display a screen for guiding a user's input, an X-ray image, a screen for displaying a state of the X-ray apparatus 100, and the like.

The controller 120 may control imaging conditions and imaging timing of the X-ray radiation device 110 according to a control command input by the user and generate a medical image based on image data received from an X-ray detector 200. The controller 120 may control a position or orientation of the X-ray radiation device 110 according to imaging protocols and a position of an object P.

The controller 120 may include a memory configured to store programs for performing the operations of the X-ray apparatus 100 and a processor or a microprocessor configured to execute the stored programs. The controller 120 may include a single processor or a plurality of processors or microprocessors. When the controller 120 includes the plurality of processors, the plurality of processors may be integrated onto a single chip or be physically separated from one another.

A holder 105 may be formed on the main body 101 to accommodate the X-ray detector 200. A charging terminal may be disposed in the holder 105 to charge the X-ray detector 200. Thus, the holder 105 may be used to accommodate and to charge the X-ray detector 200.

The input device 151, the display 152, the controller 120, and the communication unit 140 may be provided on the main body 101. Image data acquired by the X-ray detector 200 may be transmitted to the main body 101 for image processing, and then the resulting image may be displayed on the display 152 or transmitted to an external device via the communication unit 140.

The controller 120 and the communication unit 1409 may be separate from the main body 101, or only some components of the controller 120 and the communication unit 140 may be provided on the main body 101.

The X-ray apparatus 100 may be connected to external devices such as a server 191, a medical apparatus 192, and/or a portable terminal 193 (e.g., a smart phone, a tablet PC, or a wearable device) in order to transmit or receive data via the communication unit 140.

The communication unit 140 may include at least one component that enables communication with an external device. For example, the communication unit 140 may include at least one of a local area communication module, a wired communication module, and a wireless communication module.

The communication unit 140 may receive a control signal from an external device and transmit the received control signal to the controller 120 so that the controller 120 may control the X-ray apparatus 100 according to the received control signal.

Alternatively, by transmitting a control signal to an external device via the communication unit 140, the controller 120 may control the external device according to the transmitted control signal. For example, the external device may process data according to a control signal received from the controller 120 via the communication unit 140.

The communication unit 140 may further include an internal communication module that enables communications between components of the X-ray apparatus 100. A program for controlling the X-ray apparatus 100 may be installed on the external device and may include instructions for performing some or all of the operations of the controller 120.

The program may be preinstalled on the portable terminal 193, or a user of the portable terminal 193 may download the program from a server providing an application for installation. The server for providing an application may include a recording medium having the program recorded thereon.

In addition, the communication unit 140 may further include an internal communication module that enables communication between elements of the X-ray apparatus 100.

Figure 2:
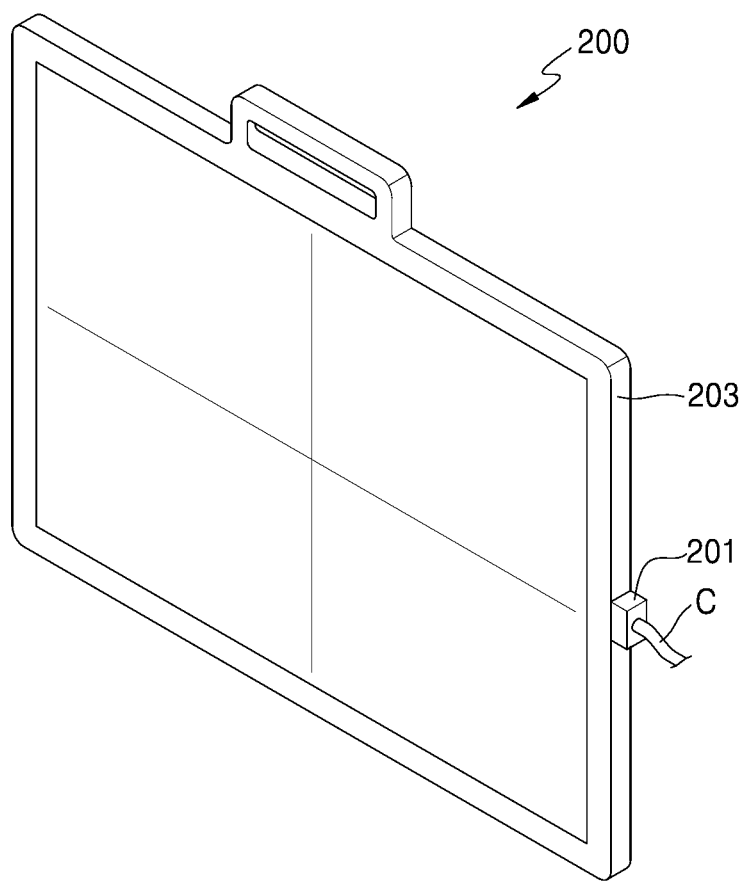
FIG. 2 is an external view of an X-ray detector according to an embodiment.

FIG. 2 is an external view of the X-ray detector 200.

As described above, the X-ray detector 200 used in the X-ray apparatus 100 may be implemented as a portable X-ray detector. The X-ray detector 200 may be equipped with a battery for supplying power to operate wirelessly, or as shown in FIG. 2, may operate by connecting a charge port 201 to a separate power supply via a cable C.

A case 203 maintains an external appearance of the X-ray detector 200 and has therein a plurality of detecting elements for detecting X-rays and converting the X-rays into image data, a memory for temporarily or permanently storing the image data, a communication module for receiving a control signal from the X-ray apparatus 100 or transmitting the image data to the X-ray apparatus 100, and a battery. Further, image correction information and intrinsic identification (ID) information of the X-ray detector 200 may be stored in the memory, and the stored ID information may be transmitted together with the image data during communication with the X-ray apparatus 100.

Figure 3:
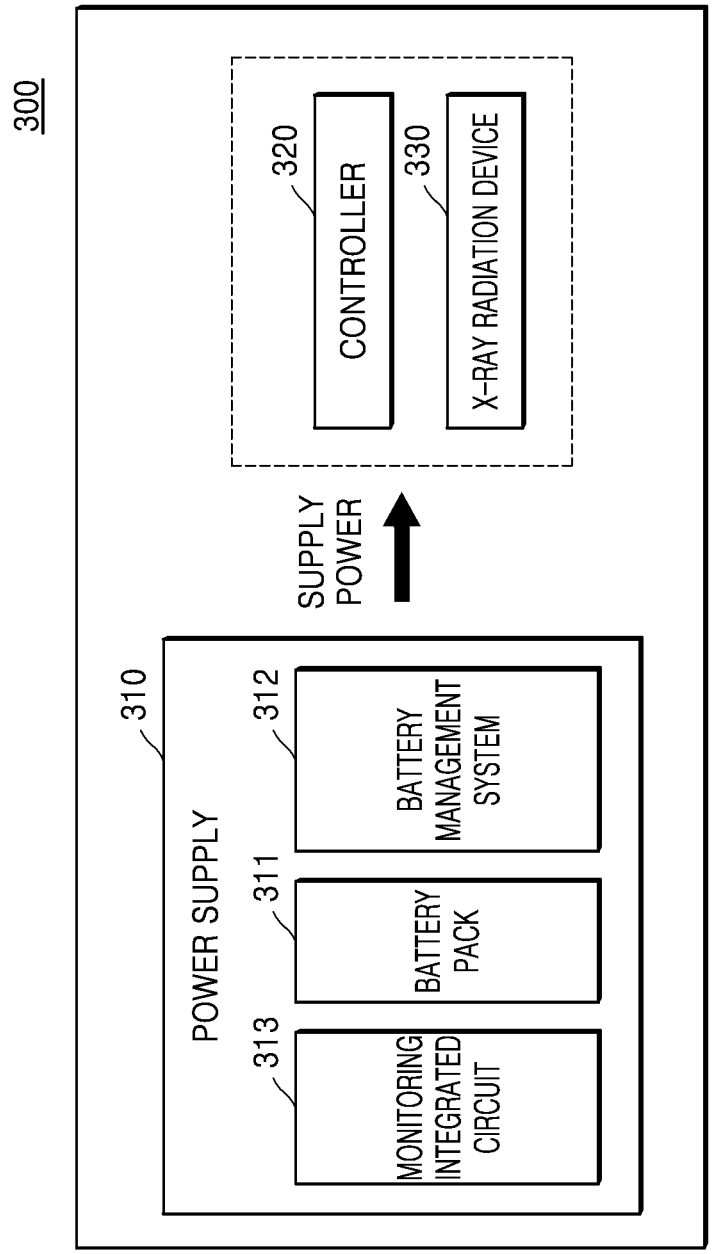
FIG. 3 is a block diagram of a mobile X-ray apparatus according to an embodiment.

FIG. 3 is a block diagram of a mobile X-ray apparatus 300 according to an embodiment.

As the mobile X-ray apparatus 300 shown in FIG. 3 corresponds to the mobile X-ray apparatus 100 described with reference to FIG. 1, descriptions same as that of FIG. 1 will be omitted.

Referring to FIG. 3, the mobile X-ray apparatus 300 may include a power supply 310, a controller 320, and an X-ray radiation device 330, and the power supply 310 may include a battery pack 311, a battery management system (BMS) 312, and a monitoring integrated circuit 313. The power supply 310 may be provided in the main body 101.

The battery pack 311 may supply operation power required for X-ray imaging to at least one component included in the mobile X-ray apparatus 300 such that the mobile X-ray apparatus 300 may perform X-ray imaging regardless of places. The at least one component may include the controller 320, the X-ray radiation device 330, an input device (not shown), an output device (not shown), and a communication unit (not shown), but is not limited thereto.

The BMS 312 may control the power supply to supply the operation power from the battery pack 311 to the at least one component of the mobile X-ray apparatus 300. That is, the BMS 312 may control and manage the power supply 310 based on a state of the battery pack 311.

The monitoring integrated circuit 313 may monitor a voltage of a plurality of battery cells. The controller 320 may control operations performed in the mobile X-ray apparatus 300 based on the operation power.

Although the BMS 312 and the monitoring integrated circuit 313 are separately shown in FIG. 3, the monitoring integrated circuit 313 may be included in the BMS 312 such that the BMS 312 controls overall operations of the monitoring integrated circuit 313.

The controller 320 may determine whether the power supply 310 is shut down. In response to a result of the determination, the controller 320 may control the monitoring integrated circuit 313 to block the monitoring power supplied from the battery cells to the monitoring integrated circuit 313. Under control of the controller 320, the monitoring integrated circuit 313 may block a monitoring current supplied from the battery pack 311.

The monitoring integrated circuit 313 may control the monitoring power supplied from the plurality of battery cells, based on whether the operation power is supplied to the at least one component of the mobile X-ray apparatus 300. More particularly, when the operation power is supplied to the controller 320 of the mobile X-ray apparatus 300, the monitoring integrated circuit 313 may receive the monitoring power from the plurality of battery cells and monitor the voltage of the plurality of battery cells. On the other hand, when the operation power is not supplied to the component of the mobile X-ray apparatus 300, the monitoring integrated circuit 313 may block the monitoring power supplied from the plurality of battery cells.

Elements of the mobile X-ray apparatus 300 and operations thereof will be described in detail with reference to FIG. 4. In addition, a detailed process in which the monitoring integrated circuit 313 blocks the monitoring power is described with reference to FIGS. 7 and 8.

Figure 4:
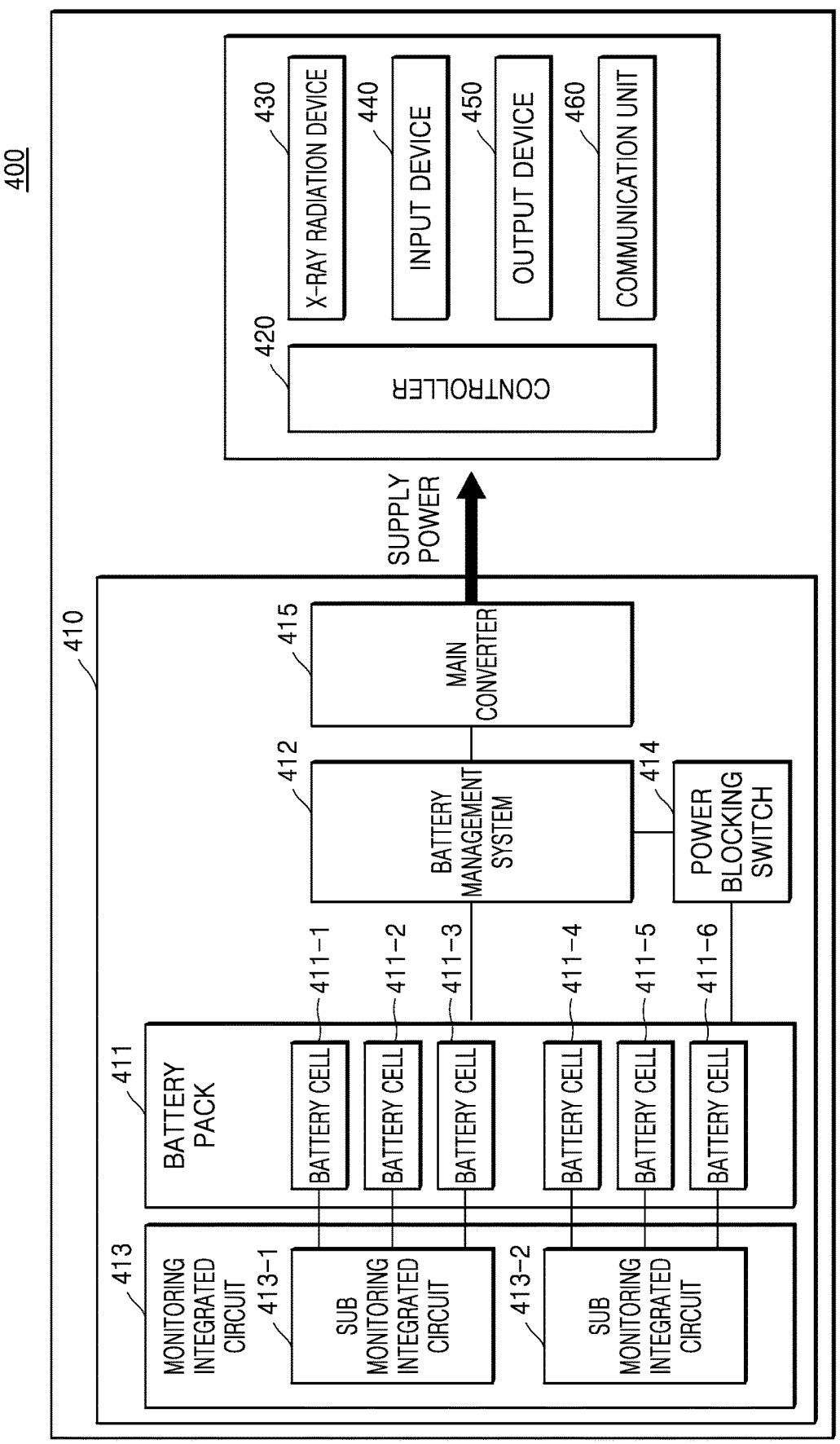
FIG. 4 is a block diagram showing a more detailed configuration of the mobile X-ray apparatus shown in FIG. 3, according to an embodiment.

FIG. 4 is a block diagram showing a more detailed configuration of the mobile X-ray apparatus 300 shown in FIG. 3, according to an embodiment.

A mobile X-ray apparatus 400 shown in FIG. 4 may correspond to the mobile X-ray apparatus 100 described with reference to FIG. 1 and the mobile X-ray apparatus 300 described with reference to FIG. 3. Therefore, regarding the mobile X-ray apparatus 400, descriptions same as those of the mobile X-ray apparatus 100 and the mobile X-ray apparatus 300 will not be given.

Referring to FIG. 4, the mobile X-ray apparatus 400 may include a power supply 410, a controller 420, an X-ray radiation device 430, an input device 440, an output device 450, and a communication unit 460. Not all elements shown in FIG. 4 are essential elements. The mobile X-ray apparatus 400 may be realized by elements more than the shown elements, or may be realized by elements fewer than the shown elements. In addition, the power supply 410 may include a battery pack 411, a BMS 412, a monitoring integrated circuit 413, a power blocking switch 414, and a main converter 415, but is not limited thereto.

The battery pack 411 may supply operation power required for X-ray imaging to at least one component included in the mobile X-ray apparatus 400.

In addition, the battery pack 411 may include a plurality of battery cells 411-1, 411-2, 411-3, 411-4, 411-5, and 411-6, and the battery cells 411-1, 411-2, 411-3, 411-4, 411-5, and 411-6 may each include an anode, a cathode, and an electrolyte. Particularly, the plurality of battery cells 411-1, 411-2, 411-3, 411-4, 411-5, and 411-6 may form a cell string in which the plurality of battery cells are serially aligned.

In addition, the battery pack 411 may be a secondary battery that may be charged and reused. For example, the battery pack 411 may include a lithium ion battery. Lithium cobalt oxide or lithium iron phosphate ($LiFePO_4$) may be used as an anode of the lithium ion battery, and graphene may be used as a cathode of the lithium ion battery. The lithium ion battery may have a structure in which a plurality of battery cells are connected and combined to one another. In addition, the lithium ion battery may include a serial combination of eighty-eight battery cells.

The BMS 412 may control the operation power to be supplied from the battery pack 411 to the at least one component of the mobile X-ray apparatus 400. In addition, the BMS 412 may detect a state of the battery pack 411, for example, a voltage or a temperature. For example, the BMS 412 may include a circuit known as a battery stack monitor that may monitor a total voltage of the battery pack 411 and a temperature of the plurality of battery cells 411-1, 411-2, 411-3, 411-4, 411-5, and 411-6 included in the battery pack 411.

The BMS 412 may operate a protection circuit for the battery pack 411 based on the state of the battery pack 411. That is, the BMS 412 may operate the protection circuit, based on the state of the battery pack 411, to prevent a dangerous state or the possibility of damage to the battery pack 411. For example, the BMS 412 may operate the protection circuit with respect to at least one of overdischarge, over-current, overheating, and unbalancing state between battery cells, based on the state of the battery pack 411. Here, the protection circuit may indicate at least one of a device, a module, and a program operated to prevent the dangerous state or the possibility of damage to the battery pack 411.

Separately from the BMS 412, the monitoring integrated circuit 413 may monitor a voltage of the plurality of battery cells. The monitoring integrated circuit 413 may transmit, to the BMS 412 or the controller 420, data or a signal related to a result of monitoring the voltage of the plurality of battery cells. In addition, the monitoring integrated circuit 413 may control the monitoring power supplied from the plurality of battery cells, based on whether the operation power is supplied to the at least component of the mobile X-ray apparatus 400.

Although the BMS 412 and the monitoring integrated circuit 413 are separately shown in FIG. 4, the monitoring integrated circuit 413 may be included in the BMS 412 such that the BMS 412 may control overall operations of the monitoring integrated circuit 413 or perform operations of the monitoring integrated circuits 413, which will be described later. Hereinafter, the BMS 412 and the monitoring integrated circuit 413 are separately described.

The controller 420 may control operations performed by the mobile X-ray apparatus 400, based on the operation power. As the controller 420 corresponds to the controller 120 described in FIG. 1, detailed description will not be given.

The controller 420 may control operations of components included in the mobile X-ray apparatus 400 to perform operations required for X-ray imaging. For example, the controller 420 may control imaging timing, imaging conditions, and the like of the X-ray radiation device 430 according to a control command input from a user, and may generate medical image data by using image data received from the X-ray detector 200. In addition, the controller 420 may also control a location or position of the X-ray radiation device 430 according to imaging protocols or a position of an object.

The controller 420 may include a memory storing a program, which executes the above-mentioned operations and the following operations, and a processor executing the stored program.

When the power supply 410 is shut down, the controller 420 may control the monitoring integrated circuit 413 such that the monitoring power that is supplied from the plurality of battery cells 411-1, 411-2, 411-3, 411-4, 411-5, and 411-6 to the monitoring integrated circuit 413 is blocked. Under control of the controller 420, the monitoring integrated circuit 413 may block a monitoring current supplied from the battery pack 411.

The power blocking switch 414 may block the operation power supplied from the battery pack 411 to the mobile X-ray apparatus 400. In an embodiment, the power blocking switch 414 may be embodied as a circuit breaker.

The main converter 415 may convert power, which is supplied from the battery pack 411, into power for the operation power of the mobile X-ray apparatus 400. The main converter 415 may be a type of DC-DC converter but is not limited thereto.

The monitoring integrated circuit 413 may monitor a voltage of a plurality of battery cells that are included in each group of a plurality of groups into which the plurality of battery cells are divided. The monitoring integrated circuit 413 may include sub monitoring integrated circuits 413-1 and 413-2 receiving monitoring power from the battery cells included in each group. A block diagram of the monitoring integrated circuit 413 shown in FIG. 4 is merely an embodiment, and the mobile X-ray apparatus 400 may include a greater number of sub monitoring integrated circuits than the sub monitoring integrated circuits 413-1 and 413-2 shown in FIG. 4.

Each of the sub monitoring integrated circuits 413-1 and 413-2 may monitor whether a voltage of a certain battery cell among the battery cells monitored by each of the sub monitoring integrated circuits 413-1 and 413-2 is discharged to be equal to or less than a certain voltage.

For example, the first sub monitoring integrated circuit 413-1 may monitor a voltage of the battery cells 411-1, 411-2, and 411-3 allocated to the first sub monitoring integrated circuit 413-1. In addition, the second sub monitoring integrated circuit 413-2 may monitor a voltage of the battery cells 411-4, 411-5, and 411-6 allocated to the second sub monitoring integrated circuit 413-2. Furthermore, the sub monitoring integrated circuits 413-1 and 413-2 may each monitor a voltage of a greater number of battery cells or a smaller number of battery cells than the number of battery cells shown in FIG. 4.

Each of the sub monitoring integrated circuits 413-1 and 413-2 may transmit, via a communication interface, data regarding a result of monitoring whether the voltage of the certain battery cell is discharged to be equal to or less than the certain voltage, to the controller 420.

In addition, each of the sub monitoring integrated circuits 413-1 and 413-2 may include a device controlling monitoring power supplied from the monitored battery cells.

For example, the device may be a switching device such as a field effect transistor (FET) device. In addition, one of ordinary skill in the art may understand that the device may correspond to a device capable of performing a switching function, in addition to the FET device mentioned above. That is, the switching device may be an arbitrary device used for blocking monitoring power supplied from the battery cells.

When the power supply 410 is shut down, the controller 420 may turn off a switching device of each of the sub monitoring integrated circuits 413-1 and 413-2 and control the monitoring power, which is supplied to each of the sub monitoring integrated circuits 413-1 and 413-2, to be blocked.

As another example, the device may be a converter that converts power, which is supplied from the main converter 415, into power for the monitoring power of a sub monitoring integrated circuit corresponding to the device. Here, the main converter 415 and the converter may be a type of DC-DC converter, but are not limited thereto. When the power supply 410 is shut down, the controller 420 may turn off the converter of each of the sub monitoring integrated circuits 413-1 and 413-2 and control the monitoring power, which is supplied to each of the sub monitoring integrated circuits 413-1 and 413-2, to be blocked.

Each of the sub monitoring integrated circuits 413-1 and 413-2 may be designed such that the monitoring power supplied to each of the sub monitoring integrated circuits 413-1 and 413-2 is separated from the operation power supplied for driving the mobile X-ray apparatus 400.

When the operation power supplied to the mobile X-ray apparatus 400 by the power blocking switch 414 is blocked, the controller 420 may determine whether the power supplied to the main converter 415 is blocked and determine whether the power supplied to the controller 420 is blocked. Based on results of the determining, the controller 420 may determine whether the operation power supplied to the at least one component of the mobile X-ray apparatus 400 is blocked.

As the X-ray radiation device 430 corresponds to the X-ray radiation device 110 described with reference to FIG. 1, detailed description will not be given.

The X-ray radiation device 430, which is used for generating X-rays and radiating the X-rays to the object, may include an X-ray source generating the X-rays and a collimator adjusting radiation areas of the X-rays generated by the X-ray source.

The input device 440 may receive, from the user, commands for operating the X-ray apparatus and various types of information regarding X-ray imaging. The input device 440 may include a keyboard, a mouse, a touch screen, a voice recognizer, a fingerprint recognizer, an iris recognizer and the like, but is not limited thereto. The controller 420 may control or operate the X-ray apparatus based on information input to the input device 440.

The output device 450 may output certain information such that the user may recognize information by using at least one of sense of touch, sense of sight, and sense of hearing. The output device 450 may output imaging-related information such as radiation of X-rays under control of the controller 420. The output device 450 may include the display 152 described with reference to FIG. 1. Alternatively, the output device 450 may include a speaker (not shown) that outputs audio signals.

When the output device 450 includes the display 152, the display 152 may display a screen for guiding user inputs, an X-ray image, a screen displaying the state of the mobile X-ray apparatus 400, and the like. The output device 450 may output, on a screen, data regarding the voltage of the monitored battery cells monitored by the BMS 412 or the monitoring integrated circuit.

The communication unit 460 may control components of the mobile X-ray apparatus 400 to perform communication with one another. The components of the mobile X-ray apparatus 400 may perform communication according to Controller Area Network (CAN) protocol, or may perform communication according to a high-speed digital interface such as Low Voltage Differential Signaling (LVDS), asynchronism serial communication such as Universal Asynchronous Receiver Transmitter (UART), a low-latency type network protocol such as error-correcting serial communication, or the like. In addition, one of ordinary skill in the art may understand that each of the components of the mobile X-ray apparatus 400 may perform communication according to a protocol method other than the above-mentioned protocols.

The mobile X-ray apparatus 400 may include a central processor to control operations of the power supply 410, the controller 420, the X-ray radiation device 430, the input device 440, the output device 450, and the communication unit 460. The central processor may be implemented as an array of a plurality of logic gates or as a combination of a general purpose microprocessor and a memory in which a program executable by the microprocessor is stored. One of ordinary skill in the art will understand that the central processor may be implemented in other forms of hardware.

Hereinafter, contents that may be clearly understood and expected by one of ordinary skill in the art may be understood as a general implementation even when each component of the mobile-X ray apparatus is not specified, and the scope of the present disclosure is not limited by a name or a physical/logical structure of a certain component.

Figure 5A:
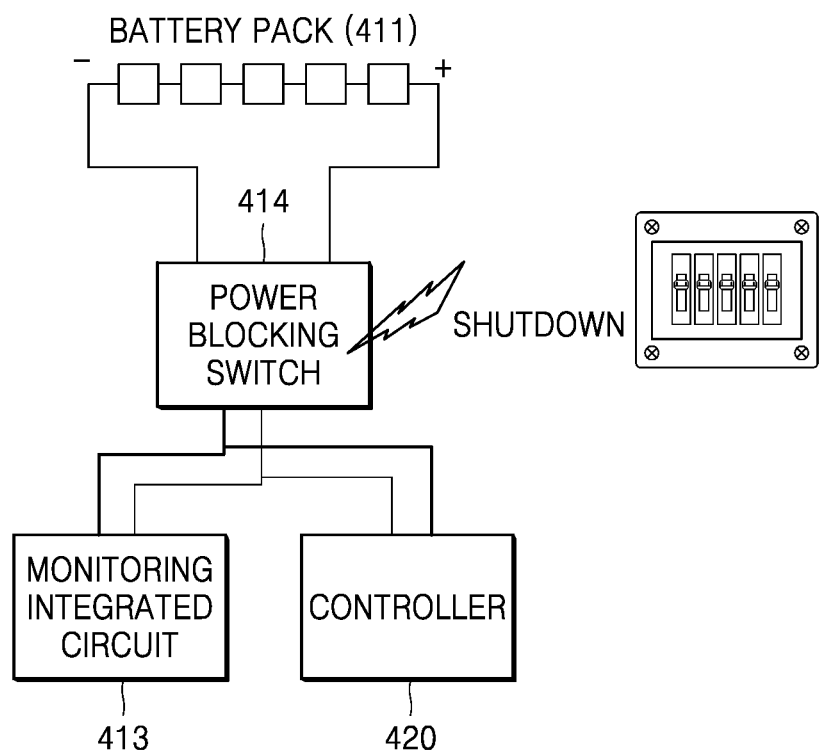
FIG. 5A is a diagram for describing power of a monitoring integrated circuit when power of a mobile X-ray apparatus is blocked by a power blocking switch, when there is one monitoring integrated circuit monitoring a voltage of battery cells, according to an embodiment.

FIG. 5A is a diagram for describing power of the monitoring integrated circuit 413 when the power of the mobile X-ray apparatus is blocked by the power blocking switch when there is one monitoring integrated circuit monitoring the voltage of the battery cells.

As shown in FIG. 5A, the battery pack 411 may include five battery cells and be connected to one monitoring integrated circuit 413. The monitoring integrated circuit 413 may monitor voltages of the five battery cells. In addition, the battery pack 411 may be connected to the controller 420 such that the operation power of the mobile X-ray apparatus 400 is supplied to the controller 420. In this case, the monitoring integrated circuit 413 and the controller 420 use same power.

Accordingly, when the power supplied to the controller 420 is blocked by the power blocking switch 414, the power supplied to the monitoring integrated circuit 413 is also blocked.

Figure 5B:
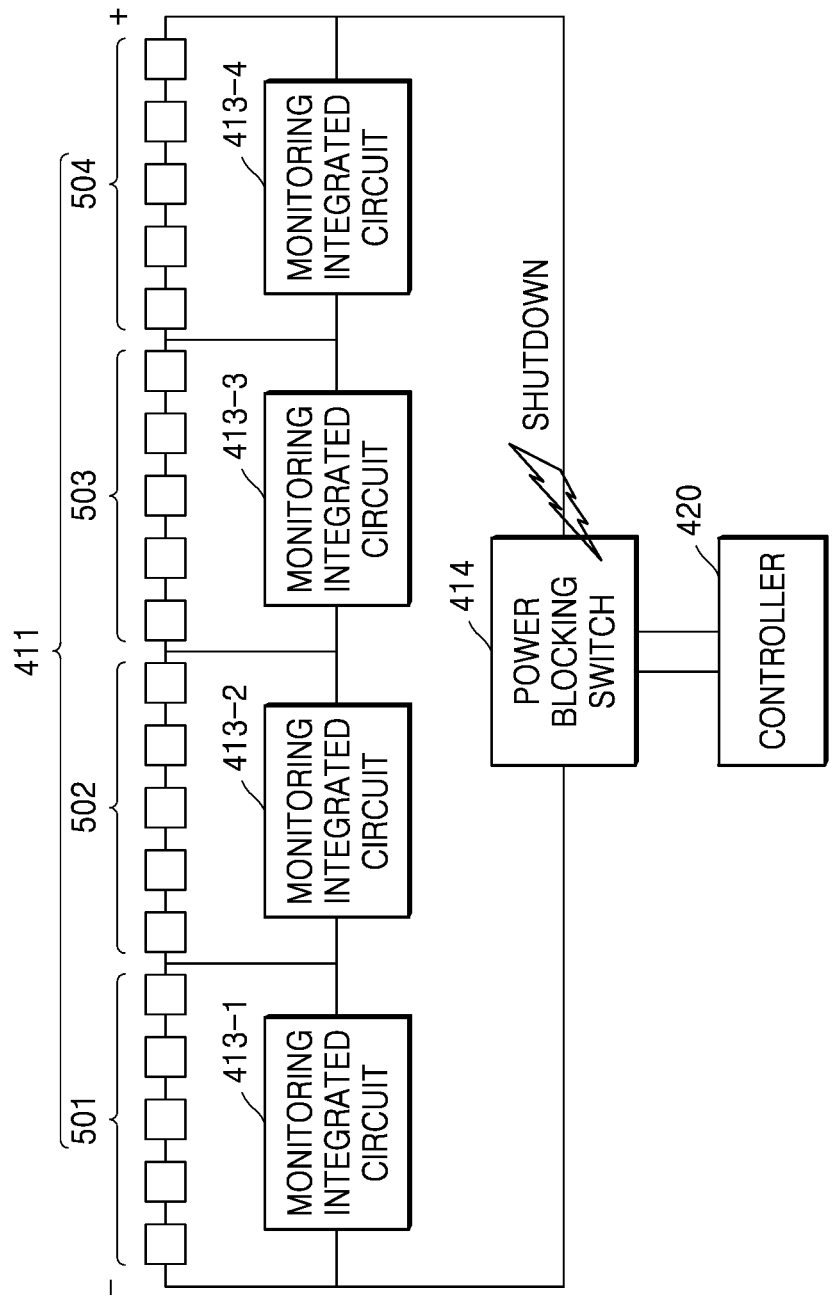
FIG. 5B is a diagram for describing power of a monitoring integrated circuit when power of a mobile X-ray apparatus is blocked by a power blocking switch when there are a plurality of monitoring integrated circuits monitoring a voltage of battery cells, according to an embodiment.

FIG. 5B is a diagram for describing the power of the monitoring integrated circuit when the power of the mobile X-ray apparatus is blocked by the power blocking switch when there are a plurality of monitoring integrated circuits monitoring the voltage of the battery cells.

As shown in FIG. 5B, the battery pack 411 may include twenty battery cells and be connected four sub-monitoring integrated circuits 413-1, 413-2, 413-3, and 413-4. The first sub monitoring integrated circuit 413-1 may monitor a voltage of battery cells 501 classified as a first group among the twenty battery cells, a second sub monitoring integrated circuit 413-2 may monitor a voltage of battery cells 502 classified as a second group among the twenty battery cells, a third sub monitoring integrated circuit 413-3 may monitor a voltage of battery cells classified as a third group among the twenty battery cells, and a fourth sub monitoring integrated circuit 413-4 may monitor a voltage of battery cells classified as a fourth group among the twenty battery cells.

In this case, power used in each of the four sub monitoring integrated circuits 413-1, 413-2, 413-3, and 413-4 are supplied from a voltage of a cell string in which battery cells respectively corresponding to the four sub monitoring integrated circuits 413-1, 413-2, 413-3, and 413-4 are serially aligned. That is, the power used in each of the four sub monitoring integrated circuits 413-1, 413-2, 413-3, and 413-4 is supplied from a partial voltage of the cell string in which the twenty battery cells are serially aligned.

In addition, the battery pack 411 may be connected to the controller 420 such that the operation power of the mobile X-ray apparatus is supplied to the controller 420. In this case, power used in the controller 420 is supplied from a total voltage of the cell string in which twenty battery cells are serially aligned.

Accordingly, as the power used in the controller 420 and the power used in each of the four sub-monitoring integrated circuits 413-1, 413-2, 413-3, and 413-4 are different from each other, even when the power supplied to the controller 420 is blocked by the power blocking switch 414, the power supplied to each of the four sub monitoring integrated circuits 413-1, 413-2, 413-3, and 413-4 is not blocked. As the power supplied to the sub-monitoring integrated circuits 413-1, 413-2, 413-3, and 413-4 is not blocked, leakage of the monitoring power occurs.

Figure 6:
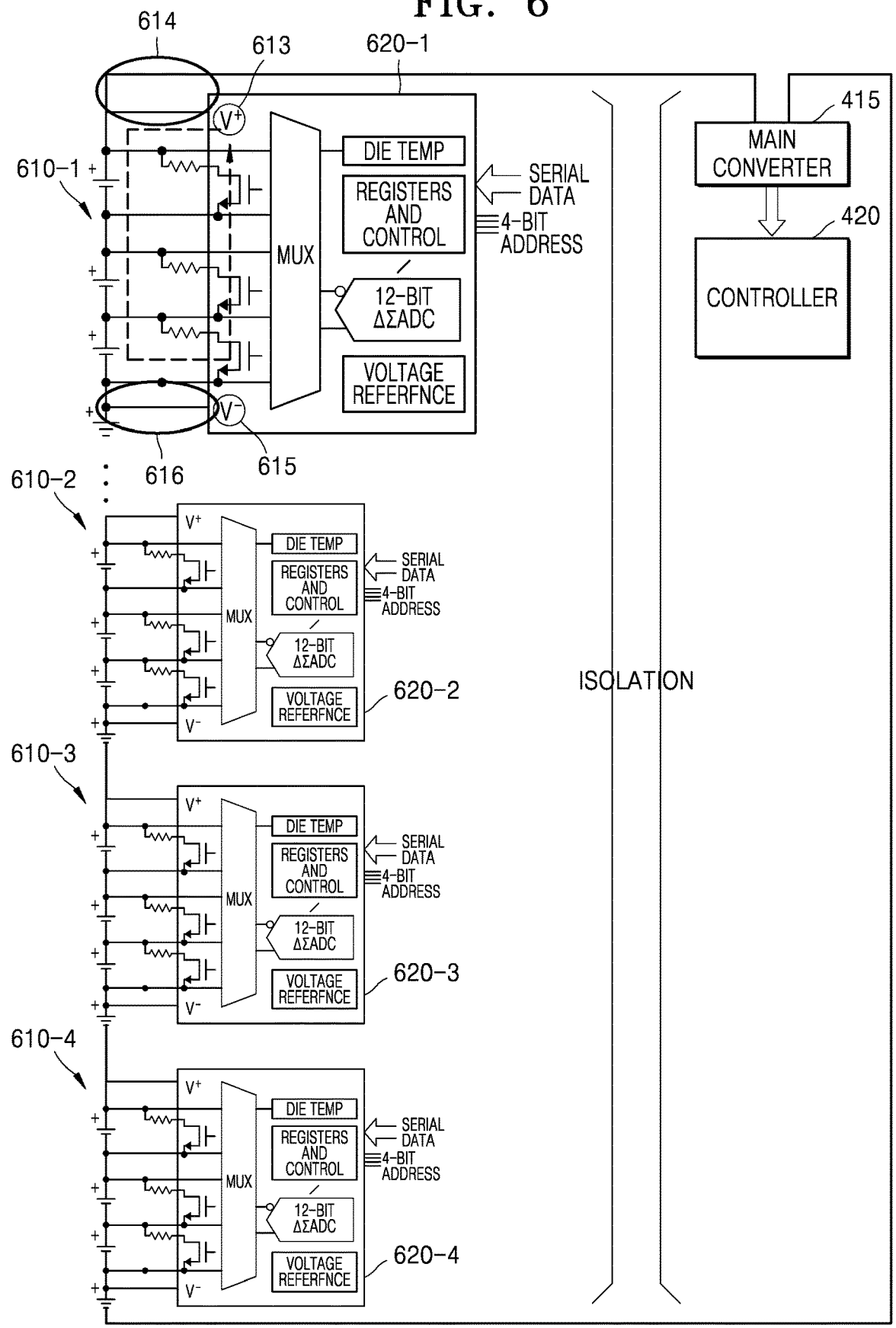
FIG. 6 is a diagram for describing a process in which power is leaked from a monitoring integrated circuit even when a power supply is shut down, according to an embodiment.

FIG. 6 is a diagram for describing a process in which power is leaked from a monitoring integrated circuit even when a power supply is shut down, according to an embodiment. One of ordinary skill in the art may understand that a circuit diagram shown in FIG. 6 is briefly illustrated to describe a process in which of power is leaked from the monitoring integrated circuit and that other devices may be included in addition to the devices that are shown such that the mobile X-ray apparatus is operated.

The battery pack 411 may include a plurality of battery cells, and the battery cells may be serially aligned and form a cell string. As the number of battery cells monitored by the monitoring integrated circuit is limited, the plurality of battery cells may be divided into a plurality of groups. That is, the monitoring integrated circuit may include a plurality of sub monitoring integrated circuits, and each of the plurality of sub monitoring integrated circuits may monitor the voltage of battery cells included in a certain group.

For example, among the plurality of battery cells, every eleven battery cells may be grouped together, and a certain sub monitoring integrated circuit may monitor a voltage of eleven battery cells included in a certain group.

As shown in FIG. 6, a first sub monitoring integrated circuit 620-1 may monitor a voltage of battery cells 610-1 allocated to the first sub monitoring integrated circuit 620-1, a second sub monitoring integrated circuit 620-2 may monitor a voltage of battery cells 610-2 allocated to the second sub monitoring integrated circuit 620-2, a third sub monitoring integrated circuit 620-3 may monitor a voltage of battery cells 610-3 allocated to the third sub monitoring integrated circuit 620-3, and a fourth sub monitoring integrated circuit 620-4 may monitor a voltage of battery cells 610-4 allocated to the fourth sub monitoring integrated circuit 620-4.

The monitoring integrated circuit requires monitoring power supply so as to monitor the voltage of the plurality of battery cells, and the monitoring power may be supplied from the plurality of battery cells. Particularly, the first sub monitoring integrated circuit 620-1 may include a (+) power input terminal and a (−) power input terminal 615. The first sub monitoring integrated circuit 620-1 may receive the monitoring power from the battery cells 610-1 allocated to the first sub monitoring integrated circuit 620-1.

The main converter 415 may convert power, which is supplied from the battery pack 411, into power for operation power of the mobile X-ray apparatus. Specifically, the main converter 415 may generate operation power of the mobile X-ray apparatus by decreasing the power supplied from the battery cells 610-1, 610-2, 610-3, and 610-4 that are serially aligned and form a cell string. The main converter 415 may provide the generated operation power to the controller 420.

In addition, as shown in FIG. 6, each of the sub monitoring integrated circuits 620-1, 620-2, 620-3, and 620-4 may be designed such that the monitoring power supplied to each of the sub monitoring integrated circuits 620-1, 620-2, 620-3, and 620-4 is isolated from the operation power supplied to the controller 200 to drive the mobile X-ray apparatus 400.

When the power supply 410 is shut down, the power supplied to the main converter 415 is also blocked. When the power supplied to the main converter 415 is blocked, the power supplied to the controller 420 is also blocked. That is, when the power supply 410 is shut down, the mobile X-ray apparatus is turned off.

However, referring to a connection structure between the first sub monitoring integrated circuit 620-1 and the battery cells 610-1 allocated to the first monitoring integrated circuit 620-1 shown in FIG. 6, the battery cells 610-1 are connected to the (+) power input terminal 613 and the (−) power input terminal 615. Due to structures 614 and 615 in which the battery cells 610-1 are directly connected to the (+) power input terminal 613 and the (−) power input terminal 615, even when the power supply 410 is shut down and the power supplied to the controller 420 is blocked, the first sub monitoring integrated circuit 620-1 may discharge the voltage of the battery cells 610-1 allocated to the first sub monitoring integrated circuit 620-1. Likewise, the other sub monitoring integrated circuits 620-2, 620-3, and 620-4 may also discharge the voltage of the battery cells 610-2, 610-3, and 610-4 respectively allocated to the sub monitoring integrated circuits 620-2, 620-3, and 620-4. In an abnormal case, deep discharge may occur in the battery cells.

Therefore, when the power supply 410 is shut down and the power supplied to the controller 420 is blocked, it is required that the monitoring power supplied to each of the sub monitoring integrated circuits is blocked. A method of blocking the monitoring power supplied to the monitoring integrated circuit when the power supply 410 is shut down will be described with reference to FIGS. 7 and 8.

Figure 7:
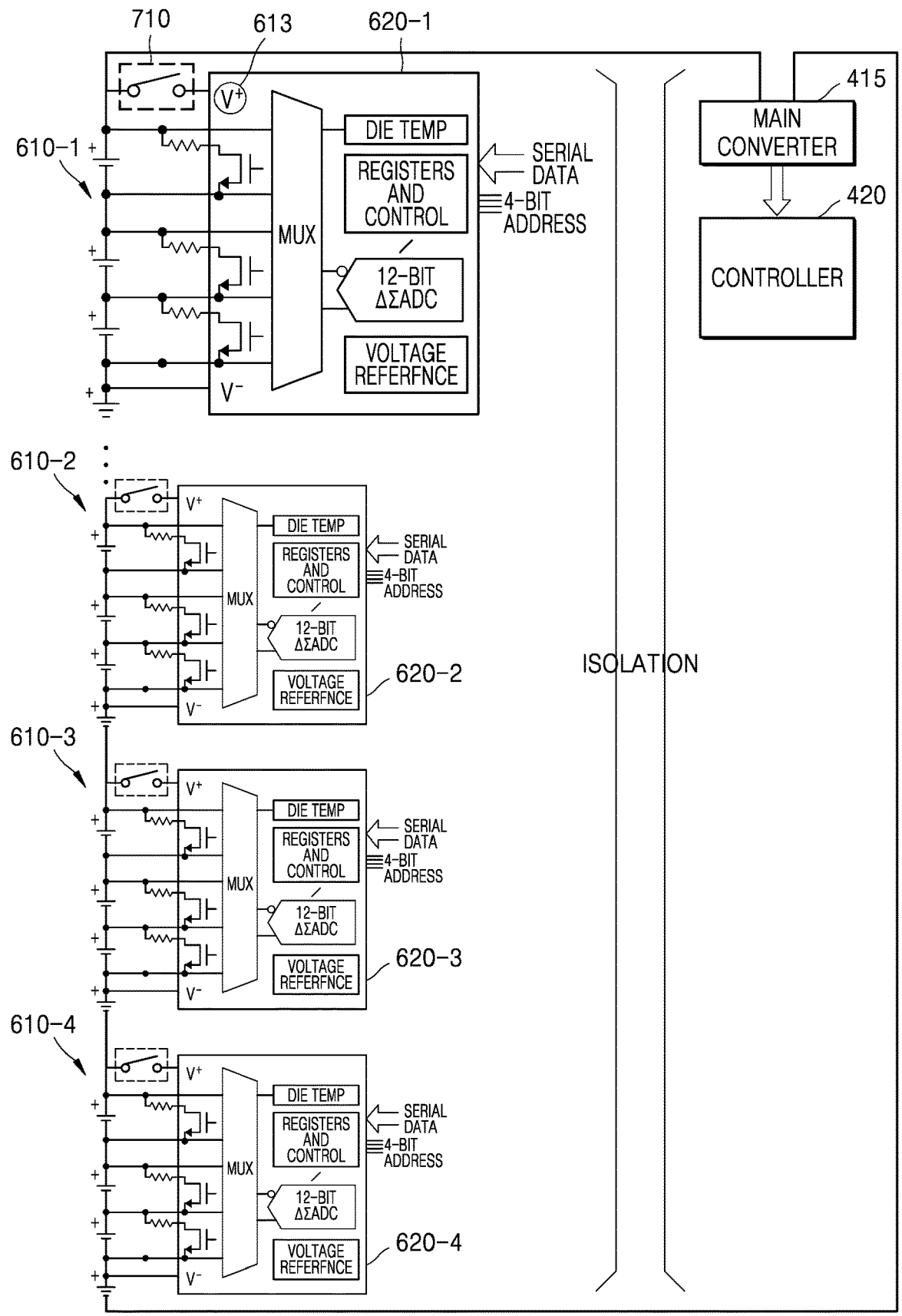
FIG. 7 is a diagram for describing a process in which power is blocked in a monitoring integrated circuit as a power supply is shut down, according to an embodiment.

FIG. 7 is a diagram for describing a process in which power is blocked in a monitoring integrated circuit as a power supply is shut down, according to an embodiment. One of ordinary skill in the art may understand that a circuit diagram shown in FIG. 7 is briefly illustrated to describe a process in which the power is blocked in the monitoring integrated circuit and other devices may be included in addition to devices that are shown such that the mobile X-ray apparatus is operated.

When a total voltage of the cell string with respect to the plurality of battery cells that are serially aligned falls within a certain range of an input voltage allowable in the monitoring integrated circuit, the mobile X-ray apparatus may control the power supplied to the monitoring integrated circuit, according to the circuit diagram shown in FIG. 7.

The circuit diagram shown in FIG. 7 is different from a circuit diagram shown in FIG. 6 in that a switching device is added between the (+) power input terminal of the sub monitoring integrated circuit and battery cells allocated to the sub monitoring integrated circuit. Particularly, the first sub monitoring integrated circuit 620-1 may include a switching device 710 to control blocking or supplying of the monitoring power that is applied from the battery cells 610-1 allocated to the first sub monitoring integrated circuit 620-1. Here, the switching device 710 may have an open and close function of a circuit and be a switching device such as a FET. One of ordinary skill in the art may understand that the device, in addition to the above-mentioned FET device, may correspond to a device capable of performing a switching function. That is, the switching device may be an arbitrary device used for blocking monitoring power supplied from the battery cells.

Likewise, the other sub monitoring integrated circuits 620-2, 620-3, and 620-4 may also include switching devices to control blocking or supplying of the monitoring power applied from the battery cells 610-2, 610-3, and 610-4 respectively allocated to the sub monitoring integrated circuits 620-2, 620-3, and 620-4.

In addition, as shown in FIG. 7, each of the sub monitoring integrated circuits 620-1, 620-2, 620-3, and 620-4 may be designed such that the monitoring power supplied to each of the sub monitoring integrated circuits 620-1, 620-2, 620-3, and 620-4 is isolated from the operation power which is supplied to the controller 200 to drive the mobile X-ray apparatus 400.

When the power supply 410 is shut down, the power supplied to the main converter 415 and the power supplied to the controller 420 are blocked. The controller 420 of the mobile X-ray apparatus 400 may control the monitoring integrated circuit such that the monitoring power supplied from the plurality of battery cells is blocked.

Specifically, the controller 420 of the mobile X-ray apparatus 400 may turn off a switching device 710 of the first sub monitoring integrated circuit 620-1 and control the monitoring power, which is supplied from the battery cells 610-1, to be blocked. At the same time, the controller 420 of the mobile X-ray apparatus 400 may turn off the switching device of each of the other sub monitoring integrated circuits 620-2, 620-3, and 620-4 and control the monitoring power, which is supplied from the battery cells 620-2, 620-3, and 620-4, to be blocked.

Figure 8:
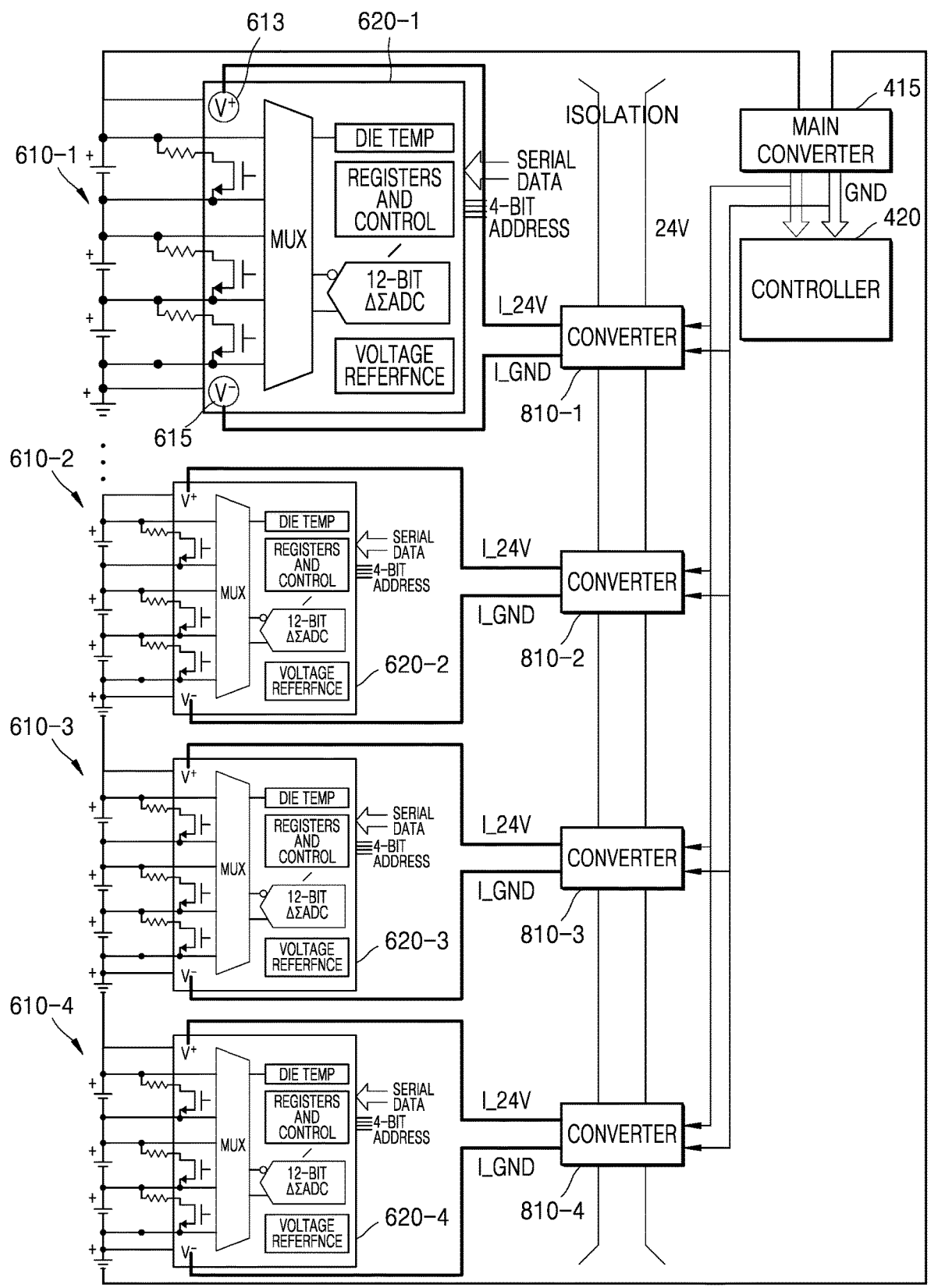
FIG. 8 is a diagram for describing a process in which power is blocked in a monitoring integrated circuit as a power supply is shut down, according to another embodiment.

FIG. 8 is a diagram for describing a process in which power is blocked in a monitoring integrated circuit as a power supply is shut down, according to another embodiment. One of ordinary skill in the art may understand that a circuit diagram shown in FIG. 8 is briefly illustrated to describe a process in which the power is blocked in the monitoring integrated circuit and other devices may be included in addition to devices that are shown such that the mobile X-ray apparatus is operated.

When the total voltage of the cell string with respect to the plurality of cells that are serially aligned does not fall within the range of the input voltage that is allowable in the monitoring integrated circuit, the mobile X-ray apparatus may control the power supplied to the monitoring integrated circuit according to the circuit diagram shown in FIG. 8.

The circuit diagram shown in FIG. 8 is different from the circuit diagram shown in FIG. 6 in that the (+) power input terminal and the (−) power input terminal of the sub monitoring integrated circuit are not directly connected to the battery cells allocated to the sub monitoring integrated circuit but are connected to a converter that receives power from the main converter.

Specifically, the (+) power input terminal 613 and the (−) power input terminal 615 of the first sub monitoring integrated circuit 620-1 may be connected to a first converter 810-1. Here, the first converter 810-1 may convert power, which is supplied from the main converter, into power for monitoring power of the first sub monitoring integrated circuit 620-1. For example, the main converter 415 may receive power of 360 V from a battery pack. The first converter 810-1 may receive a decreased voltage of 24 V from the main converter 415 and supply a voltage required for monitoring via the power input terminals 613 and 615 of the first sub monitoring integrated circuit 620-1.

Likewise, the (+) power input terminals and the (−) power input terminals of the other sub monitoring integrated circuits 620-2, 620-3, and 620-4 may be connected to converters 810-2, 810-3, and 810-4 respectively allocated to the sub monitoring integrated circuits 620-2, 620-3, and 620-4.

In addition, as shown in FIG. 8, each of the sub monitoring integrated circuits 620-1, 620-2, 620-3, and 620-4 may be designed such that the monitoring power supplied to each of the sub monitoring integrated circuits 620-1, 620-2, 620-3, and 620-4 is isolated from the operation power supplied to the controller 420 to drive the mobile X-ray apparatus 400. That is, the converters 810-2, 810-3, and 810-4 respectively allocated to the sub monitoring integrated circuits 620-2, 620-3, and 620-4 may be designed in isolation with the main converter 415.

When the power supply 410 is shut down, the power supplied to the main converter 415 and the power supplied to the controller 420 are blocked. The controller 420 of the mobile X-ray apparatus 400 may control the monitoring integrated circuit such that the monitoring power supplied from the plurality of battery cells is blocked.

Particularly, the controller 420 of the mobile X-ray apparatus 400 may turn off the first converter 810-1 of the first sub monitoring integrated circuit 620-1 and control the monitoring power, which is supplied to the first sub monitoring integrated circuit 620-1, to be blocked. At the same time, the controller 420 of the mobile X-ray apparatus 400 may turn off the converters 810-2, 810-3, and 810-4 of the other sub monitoring integrated circuits 620-2, 620-3, and 620-4 to control the monitoring power, which is supplied to the battery cells 620-2, 620-3, and 620-4, to be blocked.

Figure 9:
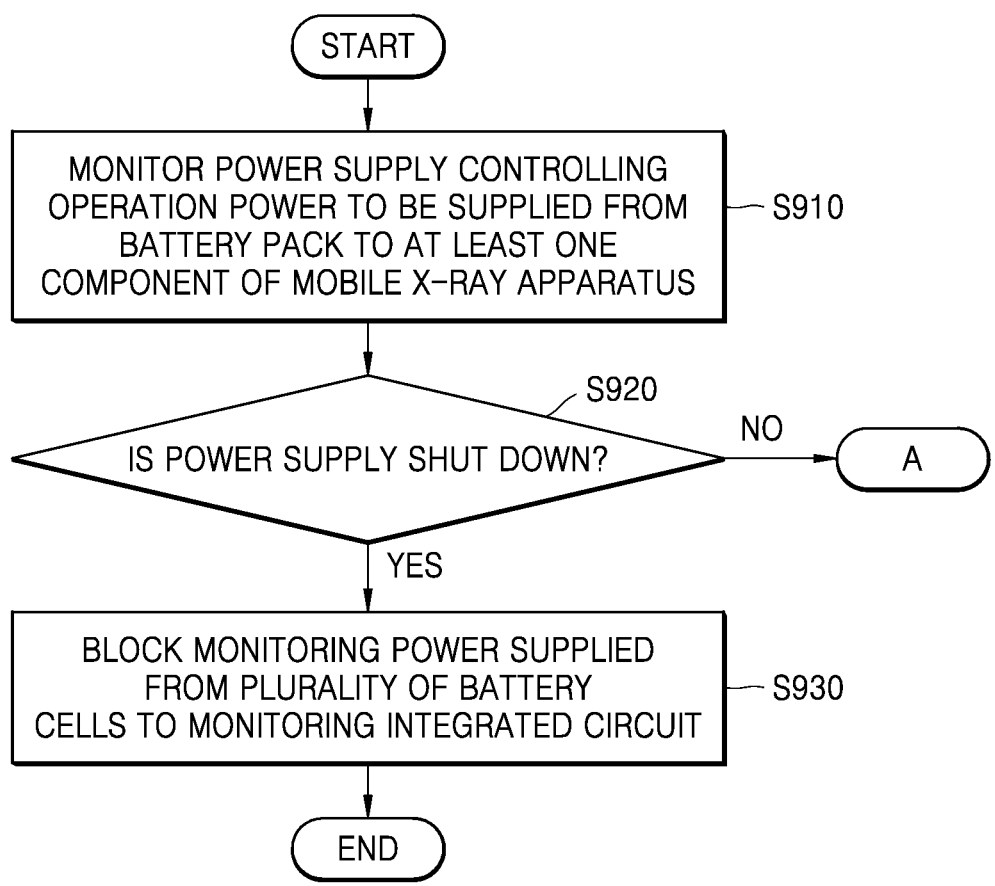
FIG. 9 is a flowchart for describing a power control method in a mobile X-ray apparatus, according to an embodiment.

FIG. 9 is a flowchart for describing a power control method in a mobile X-ray apparatus, according to an embodiment.

Operations included in the power control method in the mobile X-ray apparatus shown in FIG. 9 are to the same as operational configurations in the mobile X-ray apparatus 300 or 400 according to the embodiment of the present disclosure described with reference to FIGS. 1 through 8. Accordingly, in description of the power control method in the mobile X-ray apparatus shown in FIG. 9, descriptions same as those of the descriptions in FIGS. 1 through 8 will not be given.

The power control method shown in FIG. 9 is a power control method of a mobile X-ray apparatus including a power supply that includes: a battery pack including a plurality of battery cells, a monitoring integrated circuit monitoring a voltage of the plurality of battery cells, and a BMS, the power supply supplying operation power.

Specifically, in operation S910, the mobile X-ray apparatus may monitor the BMS that controls the operation power to be supplied from the battery pack to at least one component of the mobile X-ray apparatus.

In operation S920, the mobile X-ray apparatus may determine whether the power supply is shut down. Particularly, the mobile X-ray apparatus may determine whether the operation power is blocked by a power blocking switch. In addition, the mobile X-ray apparatus may determine whether the power supplied to a main converter is blocked. Here, the main converter is a device converting power, which is supplied from the battery pack, to power for the operation power. In addition, the mobile X-ray apparatus may determine whether the power supplied to a controller is blocked.

When the power supply is shut down, the mobile X-ray apparatus may perform operation according to operation S930. On the other hand, when it is determined that the power supply is shut down, the mobile X-ray apparatus may perform operations according to the flowchart shown in FIG. 10.

In operation S930, the mobile X-ray apparatus may block the monitoring power that is supplied from the plurality of battery cells to the monitoring integrated circuit.

Here, the monitoring integrated circuit may monitor a voltage of a plurality of battery cells included in each group of a plurality of groups into which the plurality of battery cells are divided. In addition, the monitoring integrated circuit may include sub monitoring integrated circuits receiving monitoring power from the battery cells included in each group.

The sub monitoring integrated circuits may each include a device controlling the monitoring power supplied from the monitored battery cells.

For example, the device may be a switching device. The mobile X-ray apparatus may turn off the devices of the sub monitoring integrated circuits and control the monitoring power, which is supplied to each of the sub monitoring integrated circuits, to be blocked.

As another example, the device may be a converter that converts the power, which is supplied from the main converter, into the power for the monitoring power of the sub monitoring integrated circuit corresponding to the device. Here, the main converter is a device converting power, which is supplied from the battery pack, to the power for the operation power of the mobile X-ray apparatus. The mobile X-ray apparatus may turn off the converters of the sub monitoring integrated circuits and control the monitoring power, which is supplied to each of the sub monitoring integrated circuits, to be blocked.

Figure 10:
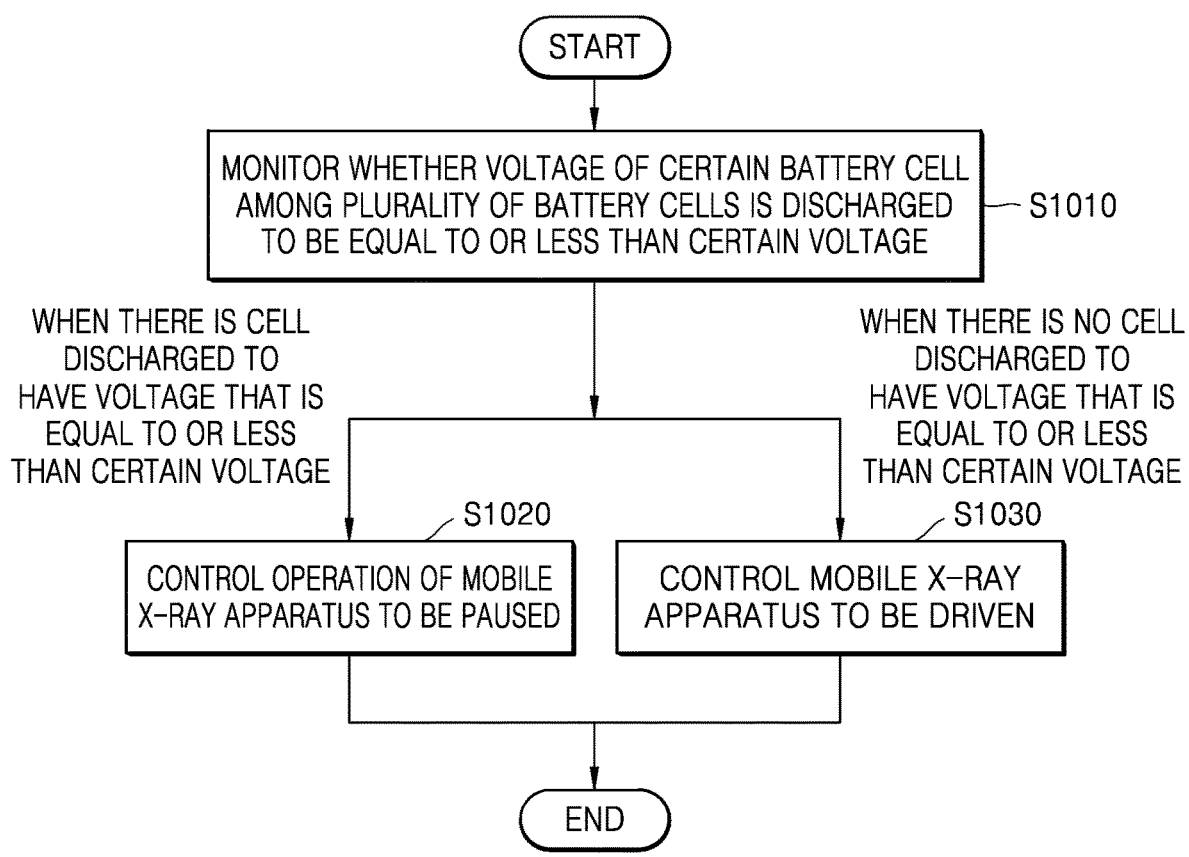
FIG. 10 is a flowchart for describing a power control method in a mobile X-ray apparatus, according to an embodiment.

FIG. 10 is a flowchart for describing a power control method in the mobile X-ray apparatus, according to an embodiment.

In operation S1010, the mobile X-ray apparatus may monitor a voltage of a certain battery cell among the plurality of battery cells. In an embodiment, the mobile X-ray apparatus may monitor whether the voltage of the certain battery cell is discharged to be equal to or lower than a certain voltage.

In operation S1020, when there is a cell discharged to have a voltage equal to or lower than the certain voltage among the plurality of battery cells, the X-ray mobile apparatus may control the operations of the mobile X-ray apparatus to be paused.

In operation S1030, when there is no cell discharged to have a voltage equal to or lower than the certain voltage among the plurality of battery cells, the mobile X-ray apparatus may continuously monitor whether the voltage of the plurality of battery cells is discharged to be equal to or lower than the certain voltage, and may control the mobile X-ray apparatus to be driven according to certain commands.

The mobile X-ray apparatuses apparatus 100, 300, 400 described above may be embodied as a hardware element, a software element, and/or a combination of a hardware element and a software element. For example, the apparatus and elements described in the embodiments may be implemented by using one or more general purpose computers or special purpose computers, for example, a processor, a controller, an arithmetic logic unit (ALU), a digital signal processor, a microcomputer, a field programmable array (FPA), a programmable logic unit (PLU), a microprocessor, or any kind of apparatuses capable of executing and responding to instructions.

Although the embodiments are described by limited embodiments and the accompanying drawings, one of ordinary skill in the art may perform various modifications and changes from the descriptions. For example, appropriate results may be achieved even when the described techniques are performed in an order different from the described order, and/or elements of the described system, structure, apparatus, and circuits are engaged or combined in an order different from the described order, or replaced or substituted by another element or equivalents thereof.

Accordingly, the scope of the present disclosure is not limited by the described embodiments and will be defined by the following claims and equivalents thereof.

The invention claimed is:

1. A mobile X-ray apparatus comprising a power supply supplying operation power, wherein the power supply comprises:
    a battery pack comprising a plurality of battery cells;
    a battery management system configured to control the operation power to be supplied from the battery pack to at least one component of the mobile X-ray apparatus; and
    a monitoring integrated circuit configured to monitor a voltage of the plurality of battery cells and control monitoring power, which is supplied from the plurality of battery cells, based on the operation powers supplied to the at least one component of the mobile X-ray apparatus.

2. The mobile X-ray apparatus of claim 1, further comprising:
    a controller configured to control an operation driven by the mobile X-ray apparatus based on the operation power and control the monitoring integrated circuit such that the monitoring power supplied from the plurality of battery cells to the monitoring integrated circuit is blocked.

3. The mobile X-ray apparatus of claim 2, wherein the monitoring integrated circuit, under control of the controller, blocks a monitoring current supplied from the plurality of battery cells.

4. The mobile X-ray apparatus of claim 2, wherein the monitoring integrated circuit monitors a voltage of battery cells that are included in each group of a plurality of groups into which the plurality of battery cells are divided, and comprises sub monitoring integrated circuits configured to receive the monitoring power from the battery cells included in each group, and each of the sub monitoring integrated circuits comprises a device configured to control the monitoring power supplied from the monitored battery cells.

5. The mobile X-ray apparatus of claim 4, wherein the device is a switching device, and the controller is further configured to determine whether the power supply is shut down, and in response to a result of the determination, block the monitoring power, which is supplied to each of the sub monitoring integrated circuits by turning off the switching device of each of the sub monitoring integrated circuits.

6. The mobile X-ray apparatus of claim 4, wherein the power supply further comprises a main converter configured to convert power, which is supplied from the battery pack, to power for the operation power of the mobile X-ray apparatus, the device is a converter configured to convert power, which is supplied from the main converter, to power for monitoring power of a sub monitoring integrated circuit corresponding to the device, and the controller is further configured to determine whether the power supply is shut down, and in response to a result of the determination, block the monitoring power, which is supplied to each of the sub monitoring integrated circuits, by turning off a converter of each of the sub monitoring integrated circuits.

7. The mobile X-ray apparatus of claim 3, wherein each of the sub monitoring integrated circuits is designed such that the monitoring power supplied to each of the sub monitoring integrated circuits is isolated from the operation power supplied to drive the mobile X-ray apparatus.

8. The mobile X-ray apparatus of claim 1, wherein the plurality of battery cells are serially aligned to form a cell string.

9. The mobile X-ray apparatus of claim 2, wherein the power supply comprises a power blocking switch configured to block operation power supplied from the battery pack to the mobile X-ray apparatus.

10. The mobile X-ray apparatus of claim 9, wherein the controller is further configured to determine whether the operation power is blocked by the power blocking switch, determines whether power supplied to the main converter, which converts the power supplied from the battery pack into power for the operation power of the mobile X-ray apparatus, is blocked, determines whether power supplied to a controller of the mobile X-ray apparatus is blocked, and determines, based on results of the determining, whether operation power supplied to at least one component of the mobile X-ray apparatus is blocked.

11. A power control method of a mobile X-ray apparatus comprising a power supply, wherein the power supply comprises a battery pack comprising a plurality of battery cells, a monitoring integrated circuit configured to monitor a voltage of the plurality of battery cells, and a battery management system, and supplies operation power, the method comprising:

monitoring the power supply that controls the operation power to be supplied from the battery pack to at least one component of the mobile X-ray apparatus;

determining whether the power supply is shut down; and in response to a result of the determination, blocking monitoring power supplied from the plurality of battery cells to the monitoring integrated circuit.

12. The power control method of claim 11, wherein the monitoring integrated circuit monitors a voltage of battery cells included in each group of a plurality of groups into which the plurality of battery cells are divided, and comprises sub monitoring integrated circuits receiving the monitoring power from the battery cells included in each group, and each of the monitoring integrated circuits comprises a device configured to control the monitoring power supplied from the monitored battery cells.

13. The power control method of claim 12, wherein the device is a switching device, and the blocking of the monitoring power comprises controlling the monitoring power supplied to each of the sub monitoring integrated circuits to be blocked by turning off a device of each of the sub monitoring integrated circuits.

14. The power control method of claim 12, wherein the power supply comprises a main converter configured to convert power, which is supplied from the battery pack, to power for the operation power of the mobile X-ray apparatus, the device is a converter configured to convert power, which is supplied from the main converter, to power for monitoring power of a sub monitoring integrated circuit corresponding to the device, and the blocking of the monitoring power comprises blocking the monitoring power, which is supplied to each of the sub monitoring integrated circuits, by turning off a converter of each of the sub monitoring integrated circuits.

15. A recording medium having recorded thereon a program comprising computer-executable instructions of a power control method of a mobile X-ray apparatus comprising a power supply, wherein the power supply comprises a battery pack comprising a plurality of battery cells, a monitoring integrated circuit monitoring a voltage of the plurality of battery cells, and a battery management system, and supplies operation power, wherein the power control method comprises:

monitoring the power supply that controls the operation power to be supplied from the battery pack to at least one component of the mobile X-ray apparatus;

determining whether the power supply is shut down; and in response to a result of the determination, blocking monitoring power supplied from the plurality of battery cells to the monitoring integrated circuit.

* * * * *